United States Patent [19]

Seko et al.

[11] Patent Number: 4,594,583

[45] Date of Patent: Jun. 10, 1986

[54] METHOD AND SYSTEM FOR DETECTION OF DRIVER DROWSINESS BY AN ABRUPT STEERING CHANGE FOLLOWING NO STEERING MOVEMENT

[75] Inventors: Yasutoshi Seko, Yokohama; Haruhiko Iizuka, Yokosuka; Takayuki Yanagishima, Yokosuka; Hideo Obara, Yokosuka, all of Japan

[73] Assignee: Nissan Motor Company, Limited, Japan

[21] Appl. No.: 580,178

[22] Filed: Feb. 15, 1984

[30] Foreign Application Priority Data

Feb. 18, 1983 [JP] Japan ................................. 58-24606

[51] Int. Cl.$^4$ ............................................. G08B 21/00
[52] U.S. Cl. ..................................... 340/576; 180/272
[58] Field of Search ..................... 340/575, 576, 52 R, 340/52 D; 180/272

[56] References Cited

U.S. PATENT DOCUMENTS 4,463,347 7/1984 Seko et al. .......................... 340/576
4,518,954 5/1985 Seko et al. .......................... 340/576

FOREIGN PATENT DOCUMENTS

54-022696 2/1979 Japan .

Primary Examiner—James L. Rowland
Assistant Examiner—Jeffery A. Hofsass
Attorney, Agent, or Firm—Lowe, Price, LeBlanc, Becker & Shur

[57] ABSTRACT

A drowsiness alarm system for a vehicle detects and signals that the vehicle driver is drowsy on the basis of the duration during which no steering adjustments are made and the magnitude and speed of abrupt steering adjustments immediately following the non-steering period. Parameters compared to the magnitude and speed of the abrupt steering adjustments in order to recognize steering behavior reflecting drowsiness are adjusted in accordance with the duration of the non-steering period.

23 Claims, 15 Drawing Figures

METHOD AND SYSTEM FOR DETECTION OF DRIVER DROWSINESS BY AN ABRUPT STEERING CHANGE FOLLOWING NO STEERING MOVEMENT

BACKGROUND OF THE INVENTION

1. Field of the Invention

The present invention relates to a drowsiness alarm system and its method of detecting and indicating that the vehicle driver is becoming drowsy on the basis of the pattern of change of a series of steering adjustments when the vehicle is moving at high speed along a road.

2. Description of the Prior Art

Various drowsiness alarm systems for vehicles have been proposed which prevent the vehicle drivers from getting drowsy in order to ensure safe driving.

Japanese Utility Model Registration Publication No. 55-121732 discloses a conventional drowsiness alarm system, the disclosure of which is incorporated by reference, wherein the system recognizes when the vehicle driver becomes drowsy and issues an alarm to the driver when first an episode of no steering adjustments exceeds a predetermined period of time and then a steering adjustment whose speed exceeds a predetermined value over a relatively wide angle of steering occurs. The disclosed system is designed on the basis of the fact that when the driver is drowsy, it is quite likely that there will be no steering adjustments for relatively long periods of time, since the driver would be unresponsive to slight deviations from the desired course, and that such periods of non-steering would be followed by abrupt and wide corrections in the course of travel of the vehicle so that the steering speed over a predetermined angle of steering would be higher than that due to course corrections during normal alert driving.

However, conventional drowsiness alarm systems may produce erroneous alarms depending on road conditions since the reference values used to recognize episodes of non-steering and to determine the steering speed are all fixed. That is to say, for example, in the case when the vehicle travels along a curved road, there is a tendency for a series of abrupt steering adjustments over a wide range of steering angle to occur after a relatively short period of no steering adjustments, and in the case where the vehicle travels along a straight road, there is a tendency for a series of abrupt steering adjustments over a narrow range of steering angle to occur after a relatively longer period of no steering adjustments.

To avoid such erroneous alarms due to the above-described conditions, a reference time used to delimit episodes of no steering adjustments may be extended and a reference time over which the steering speed over a predetermined angle of steering is measured may be shortened. However, if the system were designed as described above, the detection sensitivity would be reduced (it would become difficult to distinguish drowsiness from alertness) and early detection of drowsiness would not be achieved.

SUMMARY OF THE INVENTION

With the above-described problem in mind, it is an object of the present invention to provide a drowsiness alarm system and its detection method which detects and signals drowsiness promptly and accurately regardless of the conditions of the roads on which the vehicle runs. It is another object of the present invention to provide the drowsiness alarm system, the accuracy of which is independent of the individual differences among vehicle drivers.

It is still another object of the present invention to provide a new drowsiness alarm system and detection method.

This can be achieved by providing a drowsiness alarm system and its method wherein the reference values of the steering angle and steering speed are changed according to the duration of episodes of non-steering.

BRIEF DESCRIPTION OF THE DRAWINGS

A more complete understanding of the present invention can be obtained from the following description in conjunction with the attached drawings in which like reference numerals designate corresponding elements and in which.

DETAILED DESCRIPTION OF THE PREFERRED EMBODIMENTS

Reference will be made with the attached drawings in order to facilitate understanding of the present invention.

Figure 1:
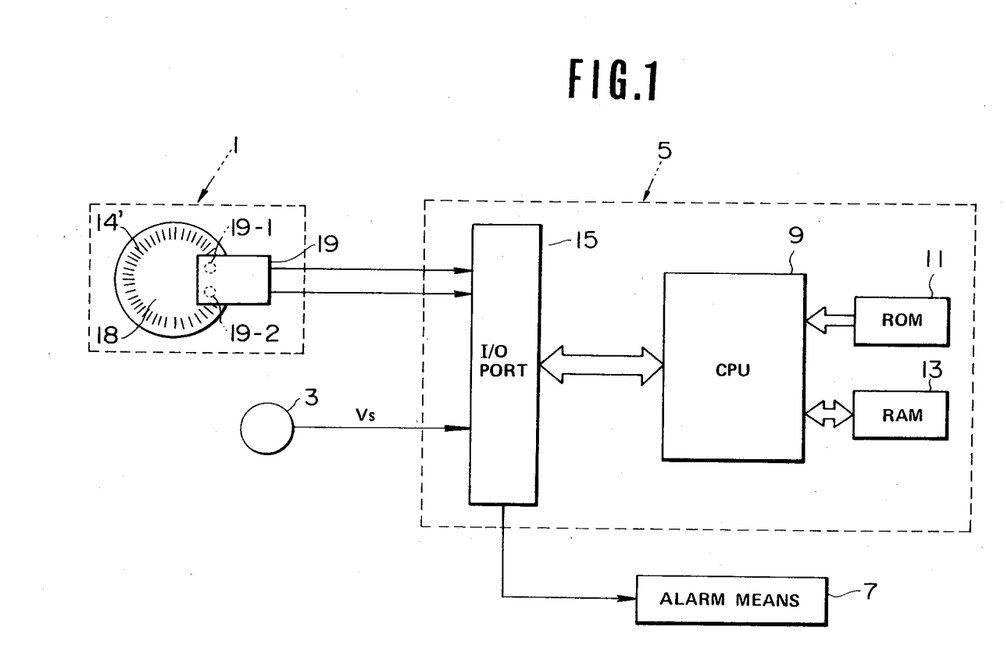
FIG. 1 shows the hardware structure of the driver drowsiness alarm system according to the present invention.
Figure 2A:
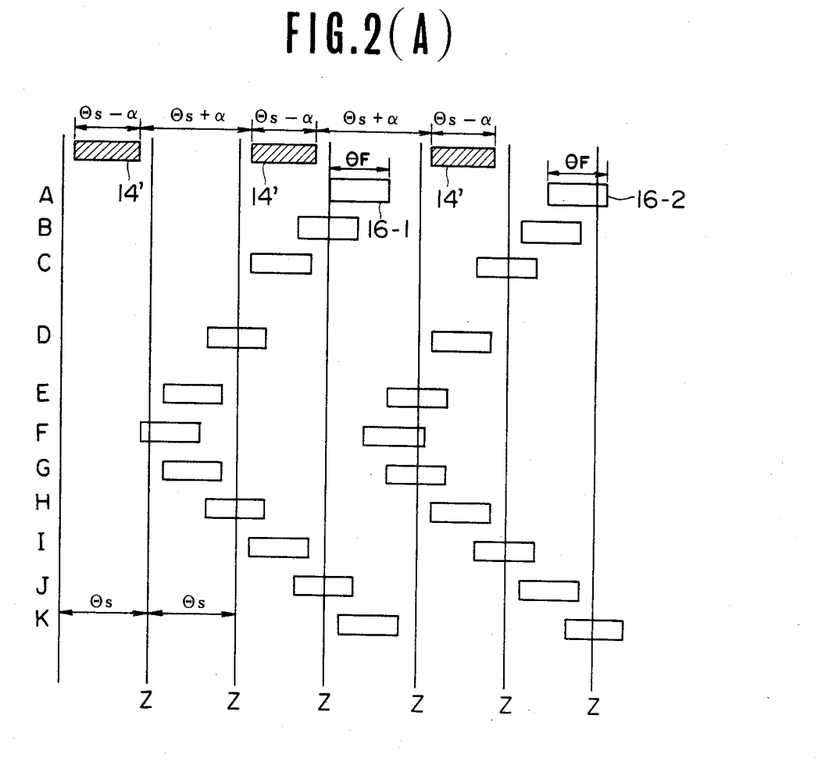
FIGS. 2(A) and 2(B) are explanatory diagrams of the output of steering angle sensor 1 shown in FIG. 1.
Figure 2B:
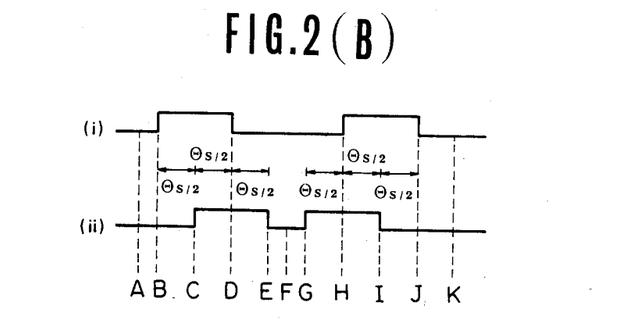

FIGS. 1, 2(A), and 2(B) show a hardware structure of a first preferred embodiment of the present invention.

In FIG. 1, numeral 1 denotes a steering angle sensor preferably attached to a steering wheel of the vehicle and numeral 5 denotes a drowsy driving detection means, which processes the output signal of the steering angle sensor 1 by way of a given processing routine according to an operational flowchart to be described later to detect whether the vehicle driver's driving behavior reflects drowsiness and actuating an alarm means 7 when detecting that the driver is indeed drowsy. The detection means 5 described above comprises a microcomputer including a Central Processing Unit (CPU) 9, a Read-Only Memory (ROM) 11, a Random-Access Memory (RAM) 13, and an Input/Output Port 15.

The structure of the steering angle sensor 1 will be described in detail below.

The steering angle sensor 1, as shown in FIG. 1 and FIG. 2(A), comprises: (a) a disk 18 which rotates with the steering wheel (not shown) and is provided with a plurality of slits 14 about its circumstance, each slit having a width of $\theta s - \alpha$ and an edge-to-edge spacing from the adjacent slit of $\theta s + \alpha$ where $\theta s$ is the center-to-center spacing; and (b) a photo interrupter module 19, electrically connected to the I/O Port 15 of the detection means 5, having a pair of photo interrupters 19-1 and 19-2 (the width of the light-transmitting slits 16-1 and 16-2 of each of the photo interrupters 19-1 and 19-2 is denoted by $\theta_F$), each for producing an electrical signal which turns on and off in response to the passage of the slits 14 of the disk 18 therethrough. It should be noted that the pair of photo interrupters 19-1 and 19-2 are arranged to be separated by an angular spacing $\{n \times \theta s + \theta s/2 \, (n=0, 1, 2, \ldots)\}$ so that they are offset by half the spacing $\theta s$ and so can resolve displacement of the steering wheel by that amount. Therefore, as shown in FIG. 2(B), the output signal waveform of the photo interrupter module 19 is a pair of (two-phase) bit-parallel rectangular waves having a phase difference of $\theta s/2$. Consequently, the direction of the rotation of the steering wheel (steering direction) can be determined according to the mode of change of the output signal of the photo interrupter module 19.

In FIG. 2(a), symbol Z denotes a boundary of the presence or absence of the output signals of the pair of photo interrupters 19-1 and 19-2.

Figure 3A:
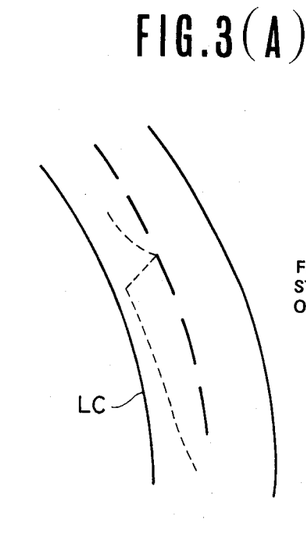
FIGS. 3(A), 3(B), 4(A) and 4(B) are diagrams illustrating two modes of detection of drowsiness by the driver drowsiness alarm system shown in FIG. 1.
Figure 3B:
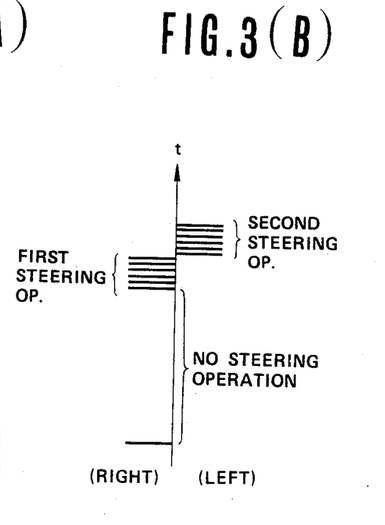
Figures 4A, 4B:
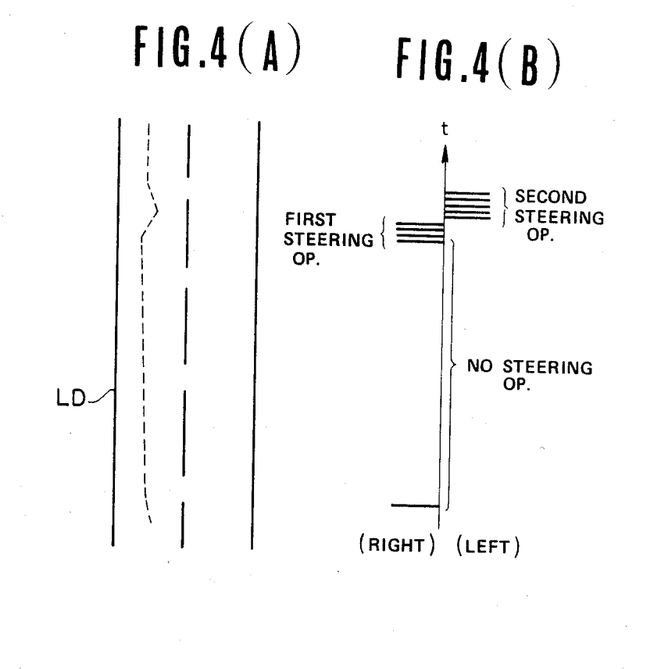

Next, the operational theory and feature of detecting steering adjustments indicating drowsiness in this embodiment will be described with reference to FIGS. 3(A), 3(B), 4(A), and 4(B). It should be noted that FIG. 3(B) and FIG. 4(B) show the signal (hereinafter referred to as steering pulses) derived from the two output signals of the steering angle sensor 1 with respect to time t and the steering pulses in the left-hand region with respect to the time axis indicate those outputted when the steering wheel is rotated clockwise while the steering pulses in the right-handed region with respect to the time axis indicate those outputted when the steering wheel is rotated counterclockwise. In addition, FIG. 3(B) corresponds to a trajectory of the vehicle running along a road shown by the dotted line of FIG. 3(A) and FIG. 4(B) corresponds to that shown by the dotted line of FIG. 4(A).

A number of steering adjustments are needed to drive the vehicle accurately along a curved road LC according to the curvature thereof. However, when the vehicle's driver gets drowsy, there is a tendency for the driver to precipitously correct the direction of the vehicle by means of the steering wheel after a relatively short period of non-steering. Such an abrupt steering correction involves a large change in steering angle over a very short time (abrupt steering). This can be appreciated from the trajectory of the vehicle shown in the dotted line of FIG. 3(A).

On the other hand, when the driver gets drowsy while driving the vehicle on a straight road LD, the driver will tend to correct the direction of the vehicle with a smaller change in steering angle after a relatively long period of non-steering. Such a steering correction involves a small change in steering angle after a longer period of non-steering than that occurring while vehicle driving along a curved road. This will be appreciated from FIG. 4(B).

In consideration of these tendencies, the drowsiness alarm system of the first preferred embodiment detects drowsiness on the basis of set drowsiness alarm conditions, the set drowsiness alarm conditions being the magnitude and rate of steering adjustments after a non-steering period.

Figure 5:
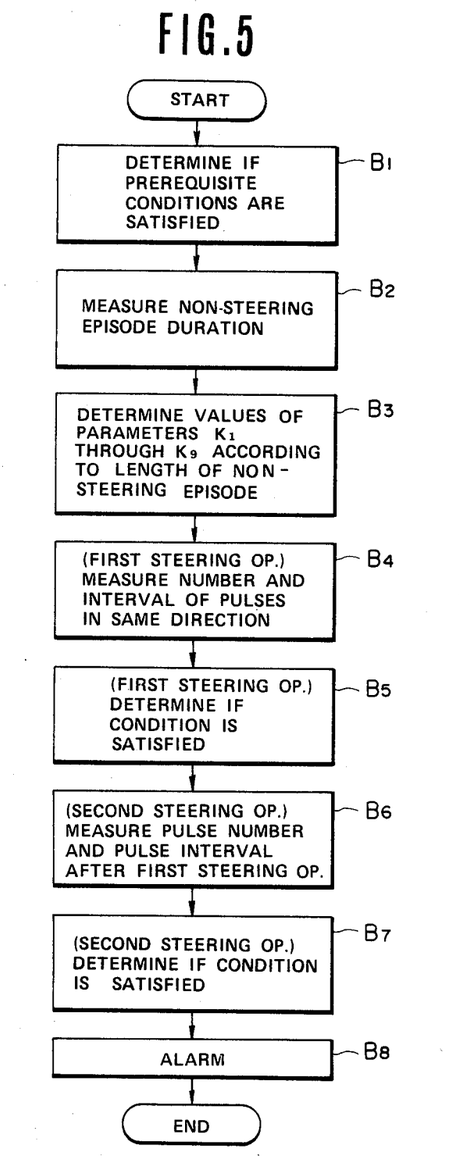
FIG. 5 is a generalized flowchart for the first preferred embodiment, illustrating the general processing procedure for detection of drowsiness.

A generalized flowchart followed by the detection means 5 for detecting drowsiness is shown in FIG. 5.

Figure 6A:
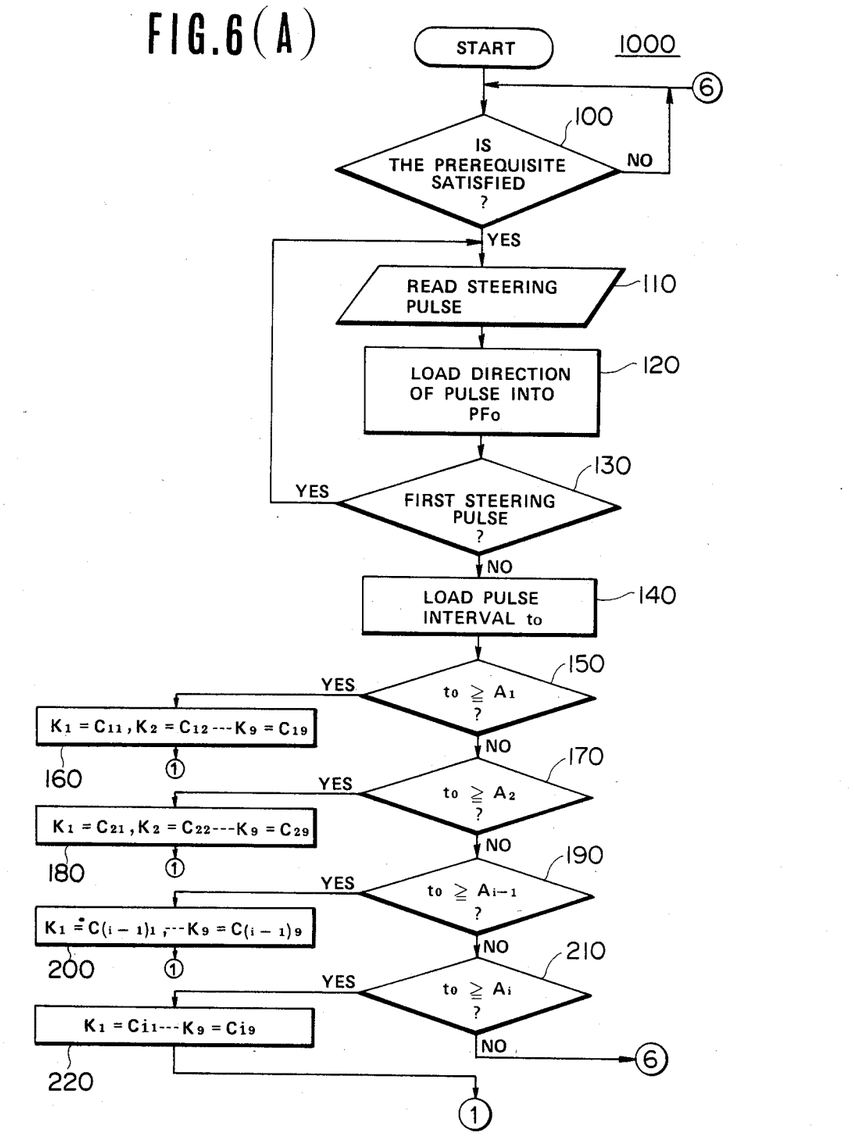
FIGS. 6(A), (B), (C) and (D) form a processing flowchart followed by the drowsy driving detection means 5 shown in FIG. 1, showing the first preferred embodiment according to the present invention.

As shown in FIG. 5, when a prerequisite condition triggering a check of the driver's drowsiness (a step 100 in a processing flowchart 1000 of FIG. 6(A) to be described later) is satisfied, the value of each of a number of parameters (in this embodiment $K_1$ through $K_9$) is set according to the measured duration of the non-steering episode (steps 110 through 220 in the same processing flowchart 1000).

First, the number of consecutive steering pulses inputted during a unidirectional steering adjustment and the interval of time during which the consecutive steering pulses are inputted are to be compared with corresponding values of the above-described parameters. Upon confirmation that the steering adjustment outlined above (hereafter referred to as first steering—also shown in FIG. 3(B) and FIG. 4(B)) has been completed (steps 230 through 400 in the above-described processing flowchart), the number of continuous steering pulses inputted during a unidirectional steering adjustment in the opposite direction and the interval of time during which the steering pulses are inputted after occurrence of the first steering are compared with corresponding values of the above-described parameters. If the above-described second steering (also shown in FIG. 3(B) and FIG. 4(B)) has been recognized to reflect drowsiness, the drowsiness alarm system issues an alarm to the drowsy driver (steps 410 through 600 in the processing flowchart 1000).

Figure 7:
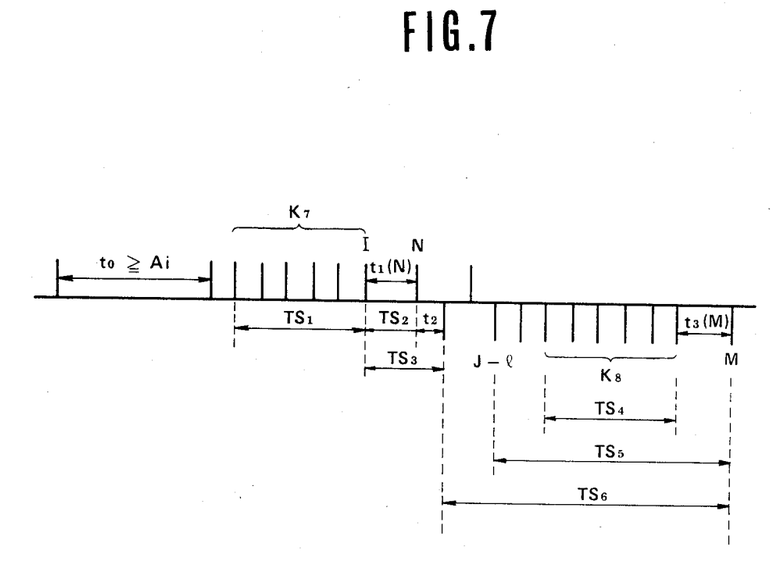
FIG. 7 is a timing chart showing a typical example of a state in which steering pulses are produced while the vehicle driver is drowsy for explaining the flowchart of FIGS. 6(A) through 6(D)

A detailed description of the processing flowchart 1000 executed by the CPU 9 shown in FIG. 1 will be given below in the case where the steering pulses shown in FIG. 7 are produced by the steering angle sensor 1 and processed by the drowsy driving detection means 5.

It should be noted that in the processing flowchart 1000, $PF_0$, $PF_1$, and $PF_2(M)$ denotes registers indicating the result of direction determination of each steering pulse read by the drowsiness detection means 5, i.e., the CPU 9, N M, I and J denote index values representing numbers of steering pulses, and $t_1(M)$, $t_1(I)$, $t_3(M)$, and $t_3(J)$ denote register arrays indexed by the given indices, each cell or register of which holds the value of the time interval between consecutive pairs of steering pulses.

A prerequisite to start detection of the steering conditions reflecting drowsiness, such as a requirement that the speed of vehicle exceeds a predetermined value, e.g., 70 km/h, is confirmed in the step 100 and thereafter the CPU a enters a wait state for the receipt of a steering pulse.

Thereafter in step 110, in response to the next steering pulse, the CPU 9 sets the register $PF_0$ in such a way that the register $PF_0$ is set to 1 when the steering pulse is derived from the clockwise direction of the steering wheel and the register $PF_0$ is set to 2 when the steering pulse is derived from the counterclockwise direction (step 120).

Next in step 130, the CPU 9 determines whether or not the last steering pulse received was the first. "First" means a steering pulse first produced after the ignition switch of the vehicle is turned on and after the condition of the step 100 is first satisfied. If it is the first steering pulse, the time at which the first steering pulse was received is recorded (this process is not shown) and the CPU 9 enters a wait state in step 110 for receipt of the subsequent steering pulse. If it is not the first steering pulse, the interval of time $t_o$ between the currently received steering pulse and the immediately preceding steering pulse is recorded (this interval of time is the duration $t_o$ of the non-steering episode) in step 140 and the CPU 9 advances to a step 150 in order to determine the duration of the non-steering episode. As the routine goes through steps 150, 170, 190, and 210 etc., the CPU 9 compares the duration of the non-steering episode $t_o$ recorded in the step 140 with reference time values $A_1$ through $A_i$ ($A_1 > A_2 > \ldots > A_i$) respectively and sets the parameter values $K_1$ through $K_9$ according to the results of the cascading comparison steps 150, 170, etc. These reference values will be shown in detail in FIG. 6 but can for now be summarized as follows: $K_1$, a characteristic time interval between pulses of the first abrupt steering adjustment; $K_2$, similar to $K_1$ but for use in the second steering adjustment; $K_3$, a characteristic total time interval for a characteristic number ($K_7$) of pulses in the first steering adjustment; $K_6$, similar to $K_3$ but for a characteristic number ($K_8$) of pulses in the second steering adjustment; $K_4$ and $K_5$, lower and upper limits respectively for the time spent in transition between the first and second steering adjustments; and $K_9$, a lower limit value for the time interval between the ends of the first and second steering adjustments. The values $K_1$ through $K_9$ can be seen to define the nature of the first and second abrupt steering adjustments with regard to driver drowsiness or alertness, and are themselves defined in relation to the nature of the immediately preceding lull or episode of non-steering. This is in keeping with the inventive concept of adjusting drowsiness recognition parameters in accordance with road conditions as indicated by the duration of non-steering periods during which the steering wheel is not noticeably turned.

If the duration of the non-steering episode $t_o$ agrees with one of the conditions defined in steps 150, 170, 190, and 210 etc., the above-described reference values $K_1$ through $K_9$ are set in the corresponding step 160, 180, 200, 220, etc. If the stored duration of the non-steering episode $t_o$ agrees with none of the conditions in the steps 150, 170, 190, and 210, i.e., $t_o < A_i$, the CPU 9 recognizes that the last steering pulse is not the result of a non-steering episode but rather is due to a steering adjustment during normal alert driving and returns control to the step 100. However, if the condition $t_o < A_i$ ($A_i$ indicates a minimum reference value of time) is not satisfied i.e. if any of the conditions 150, 170, etc. is satisfied, then there is some possibility of drowsiness and so the routine goes to steps 230 et seq. in order to determine whether a first abrupt unidirection steering adjustment described above as the FIRST STEERING is performed.

Figure 6B:
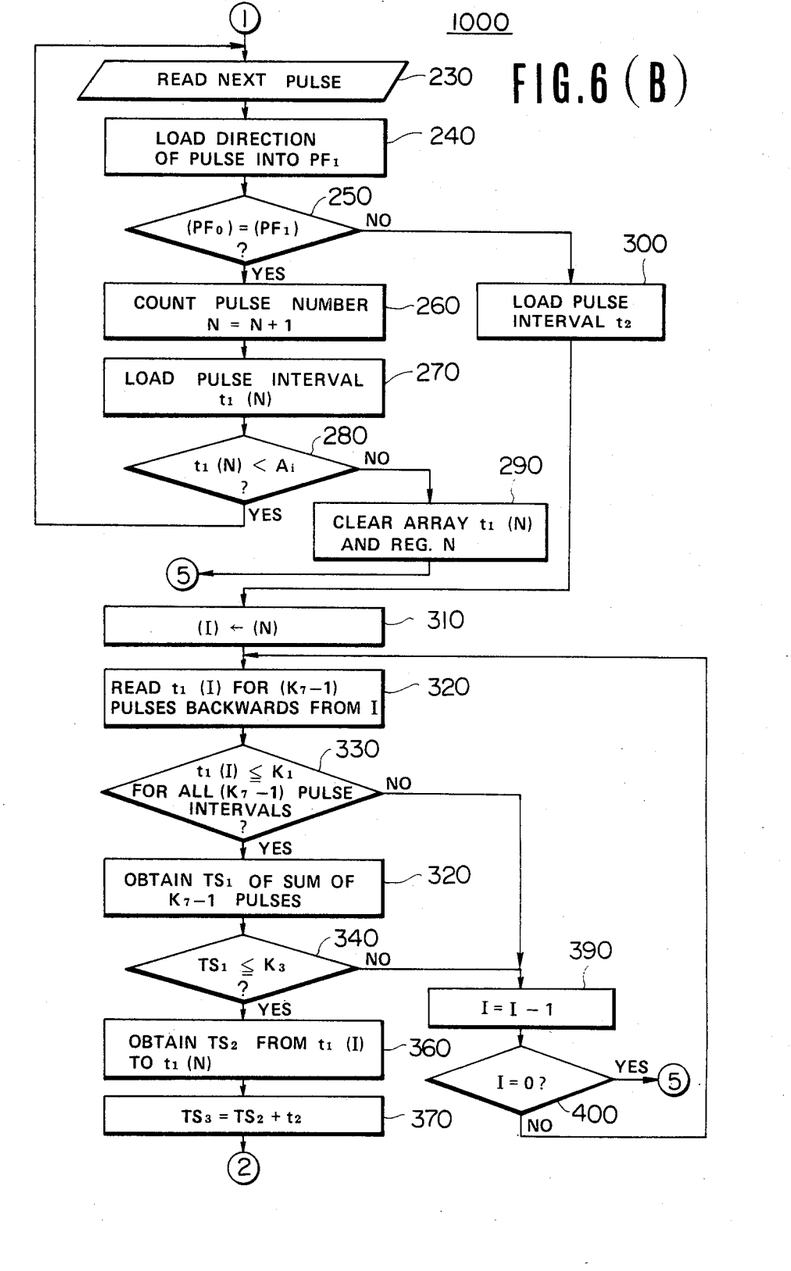

In the step 230, in response to the subsequent steering pulse after the above-described condition in steps 150, 170, 190, 210 is satisfied, the CPU 9 determines the rotational direction of the steering wheel from the input steering pulse and loads the determined rotational direction into the register $PF_1$ in step 240 in the same manner as in the step 120. Next, in step 250, the CPU 9 determines whether the steering pulse received in the step 230 and the immediately preceding steering pulse were caused by steering adjustments in the same direction of rotation. If the result is the same direction of rotation ($PF_0 = PF_1$), the routine goes to step 260. If the result is not the same ($PF_0 \neq PF_1$), the routine goes to step 300.

If the routine goes to step 260, the register N, which indicates the number of steering pulses in the same direction is incremented (N=N+1). The interval of time between the latest incoming steering pulse and the preceding steering pulse is loaded into the register $t_1(N)$ in step 270. The loaded interval of time is compared with the minimum reference time $A_i$ from among the reference times $A_1$ through $A_i$ in the next step 280. If $(t_1(N)) < A_i$ in step 280, the routine returns to the step 230 to wait for the subsequent steering pulse. If $(t_1(N)) \geq A_i$, the CPU 9 recognizes that the input steering pulse is not generated due to the above-described first abrupt unidirectional steering adjustment, i.e., the driver is not drowsy, and clears the above-described intervals of time loaded into the array $t_1(N)$ in the step 290 and the value of the register N, thus ending this cycle of driver drowsiness detection.

On the other hand, if $PF_0 \neq PF_1$ in the step 250, then the first unidirectional episode of steering adjustment has been completed within a period of time which could conceivably indicate driver drowsiness. In this case, the routine goes to step 300 in which the interval of time $t_2$ between the first pair of steering pulses in opposite directions of steering is recorded. In the next step 310, the contents of the register N incremented whenever the comparison of $PF_0 = PF_1$ is satisfied in steps 250 and 260, i.e., the number of steering pulses due to rotation of steering wheel in the first direction is decremented by one and moved into the register I, i.e., $I \leftarrow N-1$ in step 310.

Next, the CPU 9 determines whether the steering pulses derived from the rotation of the steering wheel in the first direction establish the above-described first abrupt unidirection steering condition. Toward this end, the CPU 9 starts with the most recent steering pulse interval $t_1(I)$ and works towards the first $t_1(1)$, checking first whether each interval of the last $(K_7-1)$ intervals is less than $K_1$ and if so, checking whether the sum of the checked $(K_7-1)$ intervals is less than the longer characteristic value $K_3$. If both are true the driver may be drowsy and the check routine continues. In more detail for each value of I from its current value (which drops from N−1 to 1, if necessary, as described later) to that value $-K_7$, if the recorded interval of time $t_1(I)$ is equal to or less than the first parameter value $K_1$ (, e.g., 0.25 seconds) of the input interval of time set in the steps 150 through 220, i.e., $t_1(I) \leq K_1$, the routine goes to step 340 and, on the other hand, if $t_1(I) > K_1$, the routine goes to step 390.

Figure 6C:
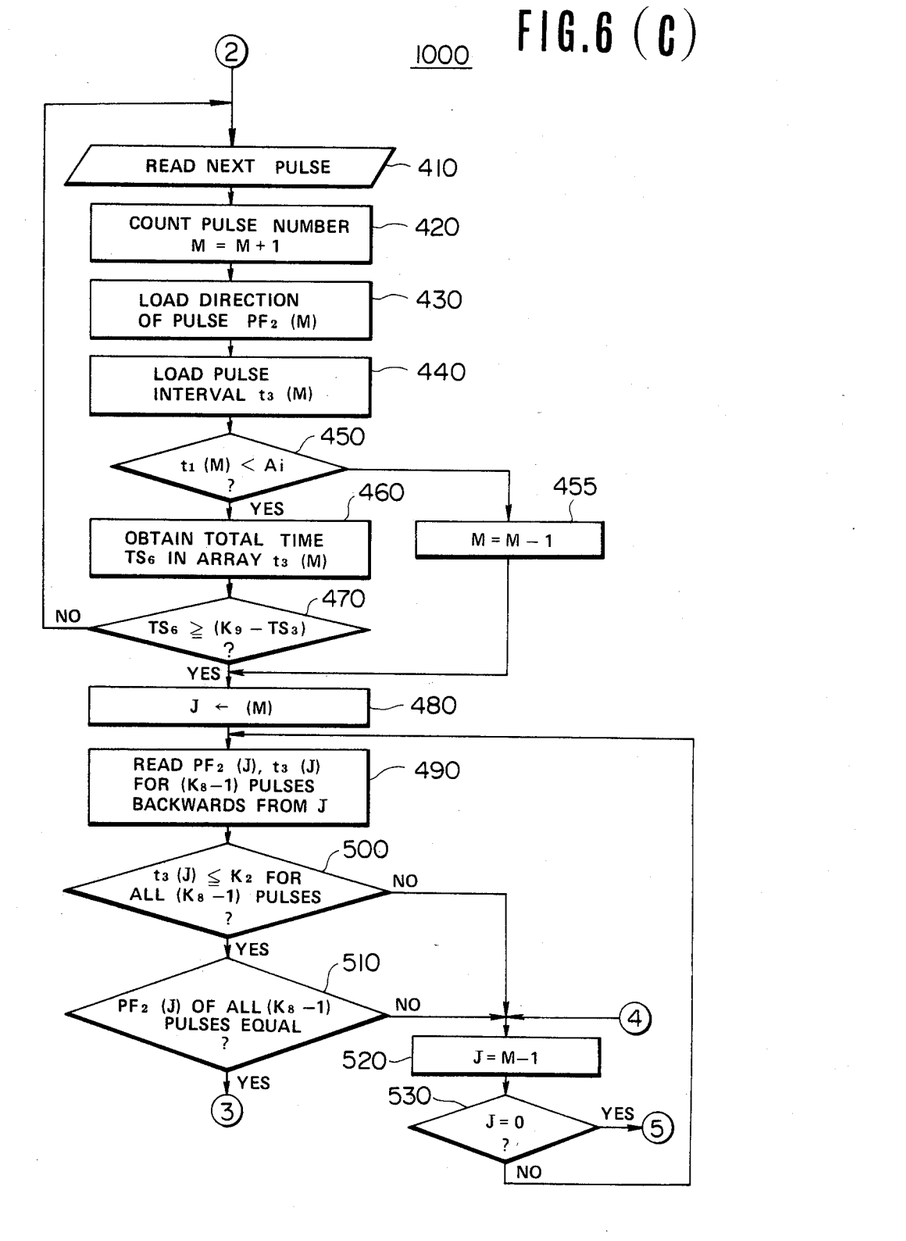

If the routine goes to the step 340, a total interval of time $TS_1$ from the last checked interval $t_1(I)$ to the last received steering pulse is derived by adding up the intervals $t_1(I)$ for I from its current value to $K_7-1$, where $K_7$ is a characteristic number of pulses in the first steering and in step operation set in steps 150–220, and in step 350 the CPU 9 compares the total time $TS_1$ with the reference value of time $K_3$ (for example, 1 second) set in the steps 150 through 220. If $TS_1 \leq K_3$, the routine goes to step 360. If $TS_1 > K_3$, the routine goes to step 390.

In step 390, the steering pulse intervals checked thus far do not indicate drowsiness but the check process of steps 320–350 are to be continued until all pulse intervals $t_1(I)$ have been checked to ensure driver alertness. Accordingly, in step 390, register I is decremented by 1 and in step 400, it is checked for I=0. If so, the routine ends; if not, steps 320–350 are repeated.

If the routine reaches step 360, then the first abrupt steering adjustment indicates that the driver may be drowsy. This would be confirmed by a second abrupt steering adjustment in the opposite direction. Thus, in order to recognize the possible occurrence of a second abrupt unidirection steering adjustment described above as the SECOND STEERING OPERATION, first a total time value $TS_2$ is obtained by adding the steering pulse intervals $t_1(I)$ for all of the steering pulses of the first steering adjustment in step 360.

After a total time $TS_3$ is obtained by adding the input interval of time $t_2$ stored in step 300 to the total time $TS_2$ in step 370, the routine goes to step 410, in which the CPU waits for the next steering pulse in order to monitor the progress of the second steering adjustment described above.

Upon receipt of a steering pulse in step 410, the value of the register M is incremented in step 420 and the result of the direction of the input steering pulses is stored in the register $PF_2(M)$ in step 430 in the same manner as in the steps 240 through 280 (except step 250). In step 440, the interval of time between the currently received steering pulse and the previously received steering pulse is stored in the register $t_3(M)$. In step 450, the CPU 9 compares the shortest reference time $A_i$ with the contents of the register $t_3(M)$. If $A_i > t_3(M)$, the routine goes to step 460. If $A_i \leq t_3(M)$, the value of the register M is decremented in step 455 and thereafter the routine goes to step 480.

In the step 460, a running total time value $TS_6$ is derived by adding the current interval stored in the array $t_3(M)$ to the previous running total $TS_6$. In step 470, the CPU 9 determines whether the obtained total time $TS_6$ exceeds a reference period of time $(K_9-TS_3)$. $K_9$ represents a reference time value (e.g. 3 seconds) from the end of first steering adjustment to the end of second steering adjustment which is set at the steps 150 through 220. $TS_3$ represents the time taken by the transient steering adjustment during transfer from the first steering adjustment to the second steering adjustment as calculated in the step 370. Thus, $(K_9-TS_3)$ represents the reference period of time required for the overall second steering adjustment itself. If $TS_6 < (K_9-TS_3)$ in the step 470, the routine returns to the step 410, having determined that the second steering adjustment is not yet adequately long. On the other hand, if $TS_6 \geq (K_9-TS_3)$, the routine goes to step 480, having determined that the second steering adjustment has proceeded adequately far, in order to further determine whether the steering pulses inputted during the total time $TS_6$ satisfy the second steering adjustment, in other words, whether the driver is drowsy.

Figure 6D:
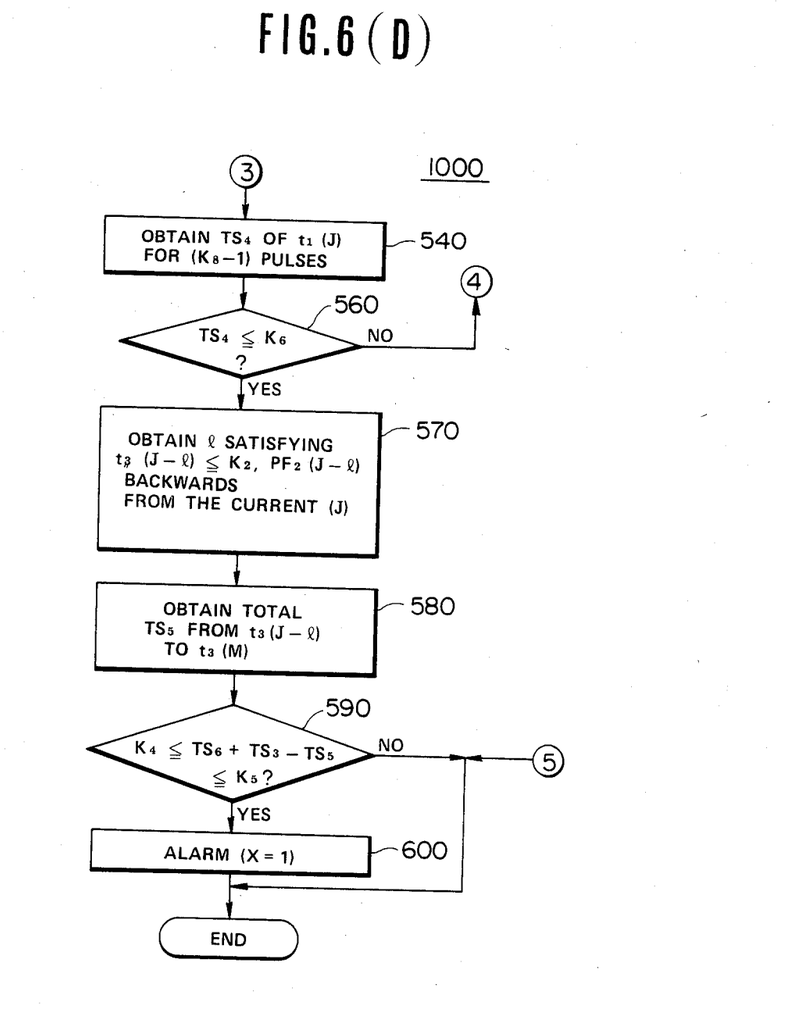

In step 480, the contents of the register M are copied into the register J.

The subsequent steps 490–560 are analogous to the loop consisting of steps 320–400 minus 360–370, in that both loops search backwards through the pulses of the corresponding steering adjustment for a series of consecutive pulses, each within a given time $(K_1, K_2)$ of its neighbors and the duration of the series overall being shorter than a given limit $(K_3, K_6)$. One difference is that in loop 490–560, an additional check is made at step 510 to ensure that all of the pulses are due to steering adjustments in the same direction. These series of pulses reflect episodes of abrupt steering correction, presumably because the driver was not adequately attentive during the preceding episode of non-steering. To maximize the reliability of this presumption, each series of pulses, i.e. each steering adjustment, must comprise a minimum number of pulses, .i.e. a minimum extent of steering correction. This prevents normal, small but abrupt steering adjustments from being interpreted as the results of drowsiness.

In more detail, at step 490, the CPU 9 uses the index J to retrieve the $PF_2$ and $t_3$ values for the last $(K_8-1)$ pulses counting backwards from the current value of J. In the next step 500, the CPU 9 determines if all of the $(K_8-1)$ retrieved intervals of time $t_3(J)$ are equal to or less than the value of reference interval of time $K_2$ (e.g., 0.25 seconds) set in the steps 150 through 220. If $t_3(J) > K_2$, the routine goes to step 520. On the other hand, if $t_3(J) \leq K_2$, the CPU 9 determines that the last steering pulses are the result of an abrupt steering adjustment and the routine goes to step 510.

In the step 510, the CPU 9 determines whether the last $(K_8-1)$ steering pulses were all due to steering changes in the same direction. If the answer is NO, i.e., if there are pulses from both directions, the routine goes to step 520. If the answer is YES, the routine goes to step 540, having determined that there is a possibility that the second steering adjustment reflects driver drowsiness. In step 540 a total time value $TS_4$ of the last $(K_8-1)$ steering pulse intervals starting from the current value of register J is obtained. Next, in step 560, the CPU 9 compares the total time $TS_4$ with the reference value of time $K_6$ (e.g., 1 second) set in the steps 150 through 220. If $TS_4 \leq K_6$, the routine goes to step 570. If $TS_4 > K_6$, the routine returns to the step 520.

In steps 500, 510 and 560, if any of the conditions $t_3(J) > K_2$, $TS_4 > K_6$ or the last $(K_8-1)$ steering pulses are not all in the same direction is true, the value of the register J is decremented in step 520. Next, in step 530, the CPU 9 determines whether the decremented value of the register J is 0. If $J \neq 0$, the routine returns to the step 490 in order to check the last $(K_8-1)$ steering pulses starting from the decremented value of the register J. If $J=0$, the routine ends since the steering pulses received after the first steering adjustment do not form a concentrate series of equidirectional pulses and so do not reflect an abrupt correction in the second direction, which would be the case if the driver were drowsy.

Subsequent steps 570–600 serve to perform a final check on the duration of the transition period between the first and second steering adjustments. If this transition interval is within a range defined in relation to the duration of the preceding episode of non-steering, then the driver is indeed steering the vehicle in manner reflecting drowsiness and an alarm is generated at step 600.

In more detail, first the total duration $TS_5$ of all of the pulses generated by the second steering adjustment must be determined and subtracted from the total end-to-end interval $(TS_6+TS_3)$ of the first and second steering adjustments. In step 570, the pulses prior to the $(J-K_8+1)$th pulse are checked to see whether or not they satisfy the conditions of the second steering adjustment, i.e. $t_3(J-1) \leq K_2$ and $PF_2(J-1)=PF_2(J)$, where $1 \geq K_8$. Then in step 580, the total duration $TS_5$ of the pulses from 1 to J is derived by summing the values $t_3(J)$, for J going from 1 to J. Next in step 590, the arithmetic expression $(TS_6+TS_3-TS_5)$ is evaluated, $TS_3$ being obtained at the step 370, $TS_6$ at the step 460, and $TS_5$ at the step 580 and the obtained value is compared with the reference values $K_4$ and $K_5$ as follows: $K_4 \leq TS_6+TS_3-TS_5 \leq K_5$. If the expression $K_4 \leq TS_6+TS_3-TS_5 \leq K_5$ is true, the CPU 9 determines that the second steering adjustment reflects drowsiness and sets a register X to "1" in step 600, which causes an alarm device 7 to operate.

Figure 8:
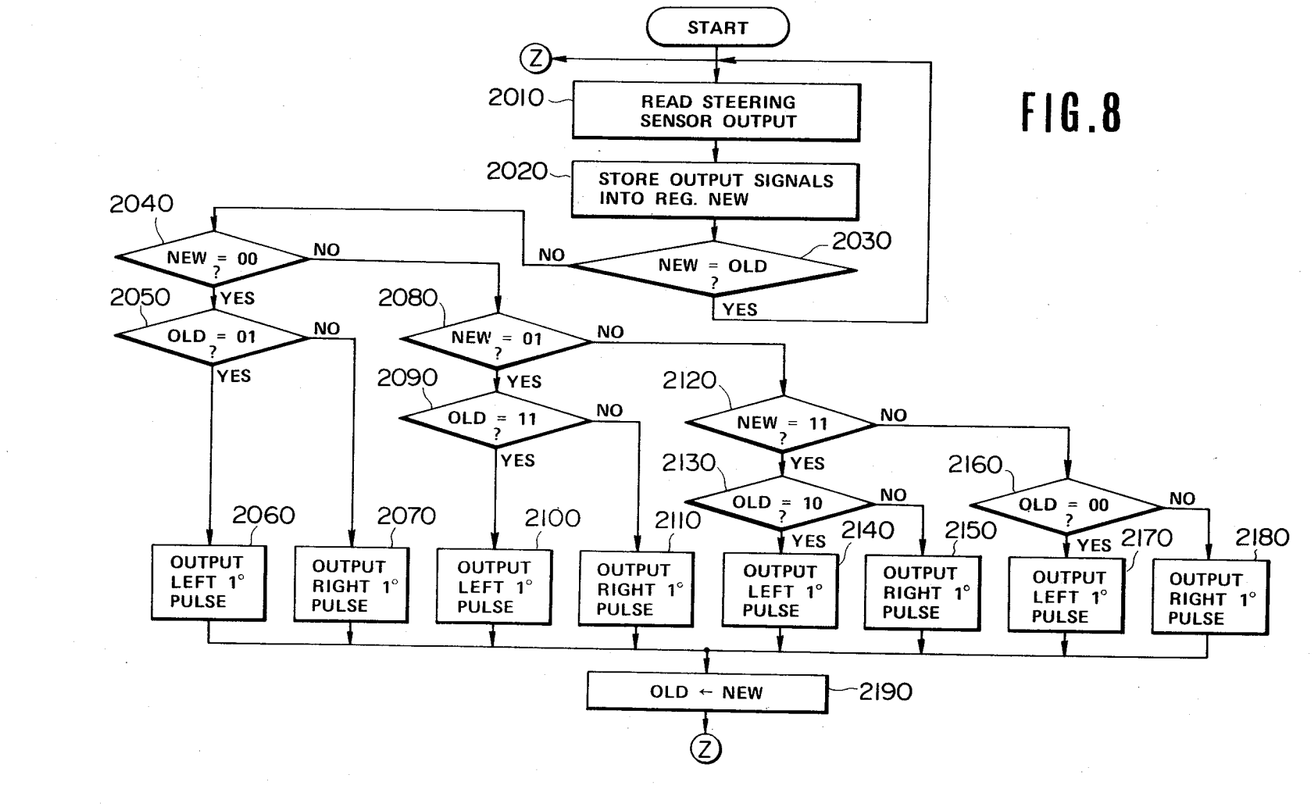
FIG. 8 is a detailed flowchart for processing a steering sensor output signal in connection with the flowchart shown in FIGS. 6(A), (B), (C) and (D)

FIG. 8 shows a detailed flowchart on the derivation of the rotational direction of the steering wheel from the steering pulses from the steering sensor 1 performed at each of the steps 120, 240, and 430 in the processing flowchart of FIG. 6.

As appreciated from FIG. 2(B), the steering sensor 1 outputs two-bit signals to the drowsiness driving detection system. The CPU 9 reads the two-bit signals and loads each two-bit signal into register NEW. In step 2030, the loaded value of the register NEW is checked to see if it agrees with the immediately preceding signal value. If the result is equality (NEW=OLD), the CPU 9 recognizes that there has been no steering adjustment and returns to the step 2010. If the result is not the same (NEW≠OLD), the CPU 9 recognizes that there has been some steering adjustment. Thereafter, the routine goes to the subsequent processing in steps 2040 through 2180 in order to determine whether the steering adjustment is derived from clockwise or counterclockwise turning of the steering wheel. The subsequent processing of steps 2040 through 2180 results in the output of a 1° pulse for either the clockwise or counterclockwise rotation of the steering wheel according to the bit state change derived from the comparison of the newly inputted two-bit signal state in the register NEW with the immediately preceding two-bit signal state in the register OLD. It should be noted that step 2190 copies the contents of register NEW into the register OLD in order to be able to refer to the latest two-bit signal for comparison with the subsequently received sensor signal.

Figure 9:
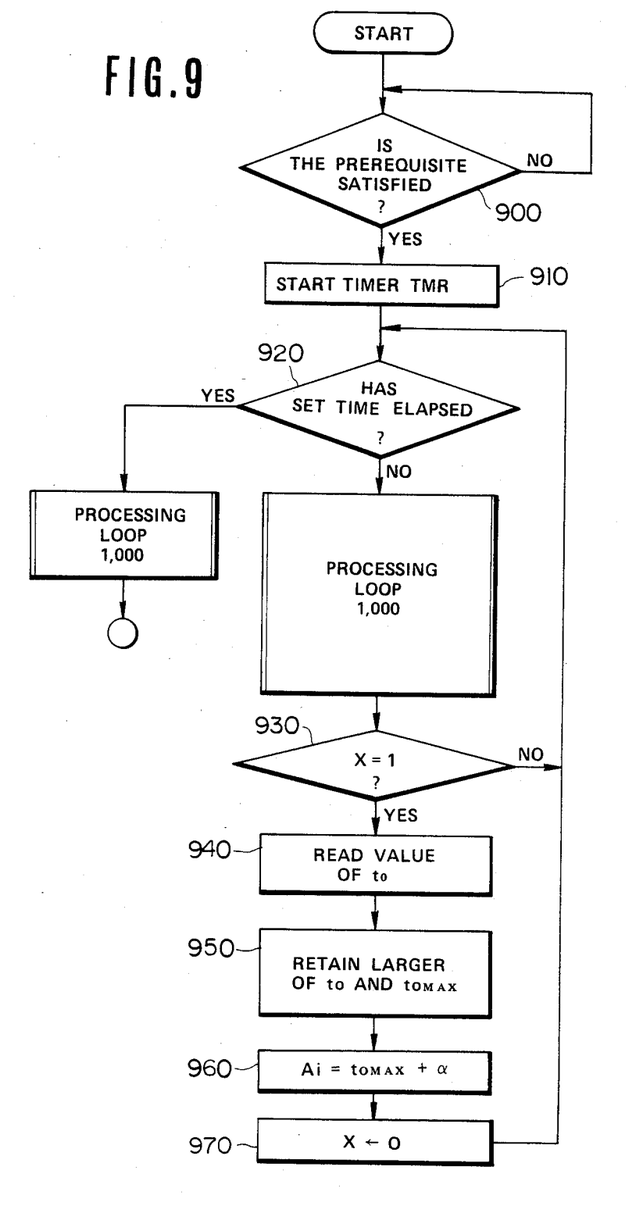
FIG. 9 is another processing flowchart for the drowsy driving detection means 5 of a second preferred embodiment.

FIG. 9 illustrates the second embodiment of the driver drowsiness detection method and system. In this embodiment, even greater flexibility and sensitivity to road conditions are added by automatically adjusting the reference times A by which the non-steering episode is evaluated, as described in more detail below. An important assumption in this case is that the driver will remain alert for at least a fixed period of time after conditions prerequisite to drowsiness detection are first satisfied, e.g. the driver will be alert for about 5 minutes after accelerating up to about 70 kph. Given this assumption, steering behavior which might indicate drowsiness is assumed not to, and the characteristic reference times A used to evaluate the duration of the non-steering episode can be adjusted upwards so that brief episodes without steering adjustments will not exceed the minimum reference time A; and so such episodes will not be interpreted as indicating drowsiness. This adjustment of the reference times A will tune the system parameters to the current road conditions and driver mood.

In more detail, after certain prerequisite conditions are satisfied in step 900, a timer TMR is activated in step 910. In subsequent step 920, the timer TMR is checked to see whether a fixed time period, e.g. 5 minutes, has elapsed. If so, control passes to the procedure 1000 outlined in FIG. 6, which then executes as described above. During the fixed time period, however, the execution of loop 1000 is modified as detailed below.

In step 930 subsequent to execution of the procedure 1000 during the fixed time period, the flag register X is checked for the value "1", which would normally indicate driver drowsiness. If X=0, then there is no indication of drowsiness and control returns to step 920. However, If X=1, the alarm device 7 is not activated as was the case in step 600 of FIG. 6(D). Rather, the duration $t_o$ of the last period without steering adjustments is read in step 940 and compared in step 950 to a value $t_{oMAX}$ representing the greatest previous duration $t_o$. If the new $t_o$ value is greater than the previous maximum $t_{oMAX}$, then $t_{oMAX}$ is replaced by the current $t_o$ value. In subsequent step 960, the minimum reference time Ai is assigned a value slightly greater than the longest non-steering interval to present, since we are assuming that steering behavior can not yet reflect drowsiness. Finally, the flag register X is reset to zero in step 970 to prevent an erroneous alarm and control returns to the step 920. Thus, the loop 920-970-920 repeats until the expiration of the set time period.

It should be noted that although only Ai is shown as being adjusted in FIG. 9, the rest of the reference times A may also be adjusted accordingly. For example, they may each be assigned new values in step 960, or they may be derived directly from Ai in steps 150-220.

As described hereinbefore, in the drowsiness alarm system according to the present invention, the detection of driver drowsiness is sensitive to the duration of a non-steering episode during which the steering wheel is turned through less than a predetermined steering angle and to the respective magnitudes of steering angle and steering speed after the aforementioned non-steering episode, and reference values of the steering angle and steering speed are changed according to the duration of the non-steering episode. The drowsiness alarm according to the present invention can detect driver drowsiness earlier and more accurately in accordance with road conditions to which the vehicle is subject than the conventional drowsiness alarm system described above.

It will be fully understood by those skilled in the art that the foregoing description is in terms of preferred embodiments wherein various modifications may be made without departing the scope of the present invention which is to be defined by the appended claims.

What is claimed is:

1. A method for detecting driver drowsiness in an automotive vehicle, comprising the steps of:
   (a) monitoring a position of a vehicular steering wheel and signalling direction and magnitude of change in the position of the steering wheel;
   (b) measuring a first duration of a period of time during which no noticeable changes in the position of the steering wheel are monitored;
   (c) determining whether said first duration of period of time measured in said step (b) is longer than any one of a plurality of given periods of time;
   (d) if said first duration is longer than one of said time periods, selecting one of a plurality of sets of predetermined conditions in accordance with said first duration;
   (e) determining whether noticeable changes in the position of the steering wheel immediately following said first duration satisfy said selected one of said plurality of sets of predetermined conditions; and
   (f) activating an alarm device indicating driver drowsiness when said first duration is determined to be longer than one of said plurality of given periods of time in said step (c) and said noticeable changes in the position of the steering wheel determined in said step (e) satisfy said selected one of said sets of predetermined conditions selected in said step (d).

2. The method of claim 1, wherein said sets of predetermined conditions include a second duration during which the position of the steering wheel is changed consistently in one direction by an amount which exceeds a first reference value.

3. The method of claim 2, wherein said sets of predetermined conditions further include a position of the steering wheel which is changed consistently in one direction at a rate greater than a second reference value during said second duration.

4. A method of detecting driver drowsiness in an automotive vehicle, comprising the steps of:
   (a) monitoring a position of a vehicular steering wheel and signalling direction, magnitude, and rate of change in the position of the steering wheel;
   (b) measuring a first duration of periods of time during which no noticeable changes in the position of the steering wheel are monitored;
   (c) measuring a second duration of periods of time during which the position of the steering wheel is changed consistently in one direction to an amount which exceeds a first reference value at a rate greater than a second reference value;
   (d) activating an alarm device indicating driver drowsiness when a period is measured in which no noticeable steering changes in the position of the steering wheel are monitored and said change in said steering wheel position in said second duration of the period immediately following said no-steering-change period exceeds said first reference value; and
   (e) adjusting at least one of said first and second reference values in accordance with said measured first duration of said no-steering-change period.

5. The method of claim 4, wherein said alarm device is activated only when, in addition to the conditions set forth in step (d), a third duration is measured of an additional period satisfying the conditions of step (c) wherein the direction of steering wheel change is opposite to that in said second duration, said third duration immediately following said second duration period, said position change in said third duration exceeding a third reference value.

6. The method of claim 5, wherein in measuring said second duration of the period satisfying the conditions of step (c), a fourth reference value is used instead of said second reference value, and said third and fourth reference values are adjusted in accordance with said measured first duration of said no-steering-change period.

7. The method of claim 4, further comprising the steps of:
   (f) monitoring an additional vehicle operation parameter and inhibiting execution of any other steps until the vehicle operation parameter satisfies a predetermined condition;
   (g) inhibitting activation of the alarm or device during a predetermined time period after the vehicle operation parameter first satisfies the predetermined condition; and
   (h) adjusting a minimum value determining no noticeable changes in the position of the steering wheel in accordance with the duration of the longest no-steering-change period during said predetermined time period.

8. The method of claim 7, wherein said minimum value is assigned a value fractionally larger than the duration of the longest no-steering-change period during said predetermined time period.

9. A system for detecting driver drowsiness in an automotive vehicle, comprising:
   (a) a first sensor means for detecting direction and magnitude of rotational movement of a vehicular steering wheel and outputting a steering pulse signal whenever said steering wheel is rotated through a predetermined angle, said steering pulse signal indicating the rotational direction of said steering wheel;
   (b) a first determination means responsive to said output signals from said first sensor means for determining whether an episode of non-steering continues for at least a set minimum interval of time based on an interval of time between two consecutive steering pulse signals derived from said first sensor means;
   (c) a second determination means for determining whether a first abrupt unidirectional steering adjustment exceeding a first predetermined angle of steering change and a first predetermined angular speed of steering change occurs, after determination by said first determination means that a non-steering episode has continued for at least said minimum interval of time, based on intervals of time between consecutive steering pulse signals indicating rotation of steering wheel in a single direction and a number of such steering pulse signals within a first predetermined interval of time, at least one value of said first predetermined angle of steering change and angular speed of steering change being adjusted according to the duration of said non-steering episode determined by said first determination means;
   (d) a third determination means for determining whether a second unidirectional abrupt steering adjustment occurs, exceeding a second predetermined angle of steering change and a second predetermined angular speed of steering change in the direction of rotation opposite said first unidirectional abrupt steering adjustment, after said first unidirectional abrupt steering adjustment determined by said first determination means, on the basis of the intervals of time between consecutive steering pulse signals indicating the same direction rotation of the steering wheel and the number of such steering pulses within a second predetermined interval of time; and
   (e) an alarm means responsive to the result of said third determination means for producing an alarm when said third determination means determines that said second unidirectional abrupt steering adjustment has occurred.

10. The system of claim 9, wherein at least one of said second predetermined angle of steering change and second predetermined angular speed of steering change is adjusted according to the duration of said non-steering episode.

11. The system of claim 9, which further comprises:
   (a) second sensor means for sensing a predetermined vehicle condition, and
   (b) means for clocking a predetermined time in response to an output signal from said second sensor means and changing said minimum interval of time set in said first determination means to a value greater than the duration of the longest non-steering episode during the clocked predetermined time.

12. The system of claim 9, wherein said first sensor means comprises:
   (a) a disk linked with the steering wheel so as to rotate with the steering wheel and having a plurality of slits arranged radially symmetrically thereabout, each slit having a width fractionally smaller than said predetermined angle of steering and the spacing between each pair of slits being fractionally greater than said predetermined angle of steering;
   (b) a pair of photo interrupters located near said disk for detecting rotation of said disk and outputting two square-pulse signals having a phase difference corresponding to a half of said predetermined angle of steering; and
   (c) a discriminator means, responsive to the two output signals from said pair of photo interrupters, for discriminating whether the steering wheel is rotating clockwise or counterclockwise depending on which of the two output signals is leading in phase and outputting said a steering pulse indicative of the discriminated result.

13. The system of any one of claims 6, 7, 8, and 9, which further comprises a second sensor means for detecting a condition prerequisite to starting detection of driver drowsiness and outputting a signal to said first determination means indicating that the prerequisite condition is satisfied.

14. The system of claim 11, wherein said second sensor means comprises a vehicle speed sensor which outputs said signal to said first determination means indicating that the vehicle speed exceeds a predetermined value.

15. A method for detecting driver drowsiness in an automotive vehicle, comprising the steps of:
   (a) monitoring a position of a vehicular steering wheel and signalling direction and magnitude of change in the position of the steering wheel;
   (b) measuring a first duration of a period of time during which no noticeable changes in the position of the steering wheel are monitored;
   (c) determining whether said first duration of period of time measured in said step (b) is longer than any one of a plurality of given periods of time;
   (d) if said first duration is longer than one of said time periods, determining whether noticeable changes in the position of the steering wheel immediately following said first duration satisfy a predetermined condition;
   (e) varying said predetermined condition for the determination of said step (d) in accordance with said first duration determined in said step (c); and
   (f) activating an alarm device indicating driver drowsiness when said first duration is determined to be longer than one of said plurality of given periods of time in said step (c) and said noticeable changes in the position of the steering wheel determined in said step (d) satisfy said predetermined condition in said step (e).

16. The system of claim 9, wherein said first, second and third determination means are comprised of a digital computer programmed to perform the functions thereof.

17. A method for detecting driver drowsiness in an automotive vehicle comprising the steps of:
   (a) detecting a period of substantially no steering operations;
   (b) detecting substantially immediately after said period of no steering operations a first steering operation in a first direction;
   (c) determining whether said first steering operation is an abrupt operation by comparing detected characteristics thereof with first predetermined criteria; and
   (d) activating an alarm means only if said first steering operation is an abrupt steering operation immediately following said period of no steering operations and is immediately followed by a second abrupt steering operation in an opposite direction.

18. A method for detecting driver drowsiness in an automotive vehicle as recited in claim 17, comprising the further steps of;
   detecting said second steering operation in said opposite direction and determining whether said second steering operation is an abrupt operation by comparing detected characteristics thereof with second predetermined criteria.

19. A method for detecting driver drowsiness in an automotive vehicle as recited in claim 17 further comprising the step of varying said predetermined criteria in accordance with a duration of said period of no steering operations.

20. A method for detecting driver drowsiness in an automotive vehicle as recited in claim 18 further comprising the step of varying at least one of said first or second predetermined criteria in accordance with a duration of said period of no steering operations.

21. A method for detecting driver drowsiness in an automotive vehicle as recited in claim 19 wherein said activating step comprises the further steps of
   determining whether said period of no steering operations exceeds a minimum predetermined duration and
   activating said alarm means only if said period exceeds said predetermined duration.

22. A method for detecting driver drowsiness in an automotive vehicle as recited in claim 21 comprising the further step of varying said minimum predetermined duration in accordance with a detected operating condition of the vehicle.

23. A method for detecting driver drowsiness in an automotive vehicle, comprising the steps of:
   (a) monitoring a position of a vehicular steering wheel and storing direction and magnitude of change in the position of the steering wheel;
   (b) measuring a first duration of a period of time during which no noticeable changes in the position of the steering wheel are monitored;
   (c) determining whether said first duration of period of time measured in said step (b) is longer than any one of a plurality of given periods of time;
   (d) if said first duration is longer than one of said time periods, selecting one of a plurality of sets of predetermined conditions in accordance with said first duration;
   (e) determining whether noticeable changes in the position of the steering wheel immediately following said first duration satisfy said selected one of said plurality of sets of predetermined conditions;
   (f) activating an alarm device indicating driver drowsiness when said first duration is determined to be longer than one of said plurality of given periods of time in said step (c) and said noticeable changes in the position of the steering wheel determined in said step (e) satisfy said selected one of said sets of predetermined conditions selected in said step (d).

* * * * *